(12) United States Patent
Sher

(10) Patent No.: US 6,475,160 B1
(45) Date of Patent: Nov. 5, 2002

(54) SKIN TESTING DEVICE

(76) Inventor: Nathan Sher, 3900 Yonge Street, Suite 701, Toronto, Ontario (CA), M4N 3N6

( * ) Notice: Subject to any disclaimer, the term of this patent is extended or adjusted under 35 U.S.C. 154(b) by 0 days.

(21) Appl. No.: 09/689,876

(22) Filed: Oct. 13, 2000

(51) Int. Cl.[7] ............................................. A61B 5/00
(52) U.S. Cl. ...................................................... 600/556
(58) Field of Search ........................................ 600/556

(56) References Cited

U.S. PATENT DOCUMENTS

| | | | |
|---|---|---|---|
| 1,619,424 A | 3/1927 | Latagliata | 128/329 |
| 2,522,309 A | 9/1950 | Simon | 128/743 |
| 3,074,395 A | 1/1963 | Kevorkian | 128/2 |
| 3,289,670 A | 12/1966 | Krug et al. | 128/743 |
| 4,483,348 A | 11/1984 | Sher | 128/743 |
| 4,711,247 A | 12/1987 | Fishman | 128/743 |
| 4,823,806 A | 4/1989 | Bajada | 128/744 |
| 5,076,282 A | 12/1991 | Fishman et al. | 128/743 |
| 5,097,810 A | 3/1992 | Fishman et al. | 128/743 |
| 5,139,029 A | 8/1992 | Fishman et al. | 128/743 |
| 5,335,670 A | 8/1994 | Fishman | 128/743 |
| 5,474,084 A | 12/1995 | Cunniff | 128/744 |
| 5,673,706 A | 10/1997 | Scott | 128/744 |
| 5,810,743 A | 9/1998 | Cronin | 600/557 |
| 5,843,114 A | 12/1998 | Jang | 606/186 |
| 5,871,452 A | 2/1999 | Baker et al. | 600/556 |
| 5,944,671 A | 8/1999 | White, Jr. | 600/556 |
| 5,964,729 A | 10/1999 | Choi et al. | 604/47 |

FOREIGN PATENT DOCUMENTS

EP 0 224 225 11/1986

Primary Examiner—Kevin Shaver
Assistant Examiner—Pamela Wingood
(74) Attorney, Agent, or Firm—Bereskin & Parr

(57) ABSTRACT

A skin testing device having a housing that supports a wheel. The wheel has a plurality of pointed tines for introducing a freeze dried allergen solution to a patient's skin. The pointed tines are located on an allergen plate that has radial grooves for receiving and containing different allergen solutions.

11 Claims, 5 Drawing Sheets

SKIN TESTING DEVICE

FIELD OF THE INVENTION

The invention relates to medical instruments and in particular to a skin testing device.

BACKGROUND OF THE INVENTION

Allergy tests are typically conducted by depositing droplets of different allergens at distinct locations on a patient's arm. The arm is then pricked with a needle at each droplet location so that an allergic reaction (if any) can be observed.

U.S. Pat. No. 4,483,348 (Sher) discloses a skin testing device that greatly simplifies the manner in which an allergen is introduced to a patient's skin. The device includes a wheel having a series of pointed tines that are each coated with a different lyophilized allergen. The wheel is rolled along the arm of a patient so that each tine pierces the skin sufficiently to allow for a reaction with the allergen deposited on each tine. The wheel is then disposed at the end of the test to avoid communicating diseases between patients.

It has been found that the application of allergen solutions to the tines of the wheel is difficult. There is a need for an improved device that allows allergens to be applied to the wheel in a cost effective manner.

SUMMARY OF THE INVENTION

In one aspect the invention provides a skin testing device comprising:

an allergen plate defining a plurality of pointed tines for piercing a patient's skin;

a plurality of grooves defined in a surface of said allergen plate for receiving an allergen solution, each one of said grooves being aligned with a corresponding one of said pointed tines;

a housing for shrouding a portion of said allergen plate;

means for rotatably supporting said allergen plate within said housing.

In another aspect the invention provides an allergen plate for a skin testing device comprising:

a body defining a plurality of pointed tines for piercing a patient's skin; and a plurality of grooves defined in a surface of said body for receiving an allergen solution, each of said grooves being aligned with one of said pointed tines.

BRIEF DESCRIPTION OF THE DRAWINGS

For a better understanding of the present invention, and to show more clearly how it may be carried into effect, reference will now be made by way of example to the accompanying drawings. The drawings show preferred embodiments of the present invention, in which.

DETAILED DESCRIPTION OF THE PREFERRED EMBODIMENTS

Referring to FIGS. 1–8, a first embodiment of a skin testing device in accordance with the present invention is shown at 20. The device includes a housing 22 that supports a wheel 24.

Figure 1:
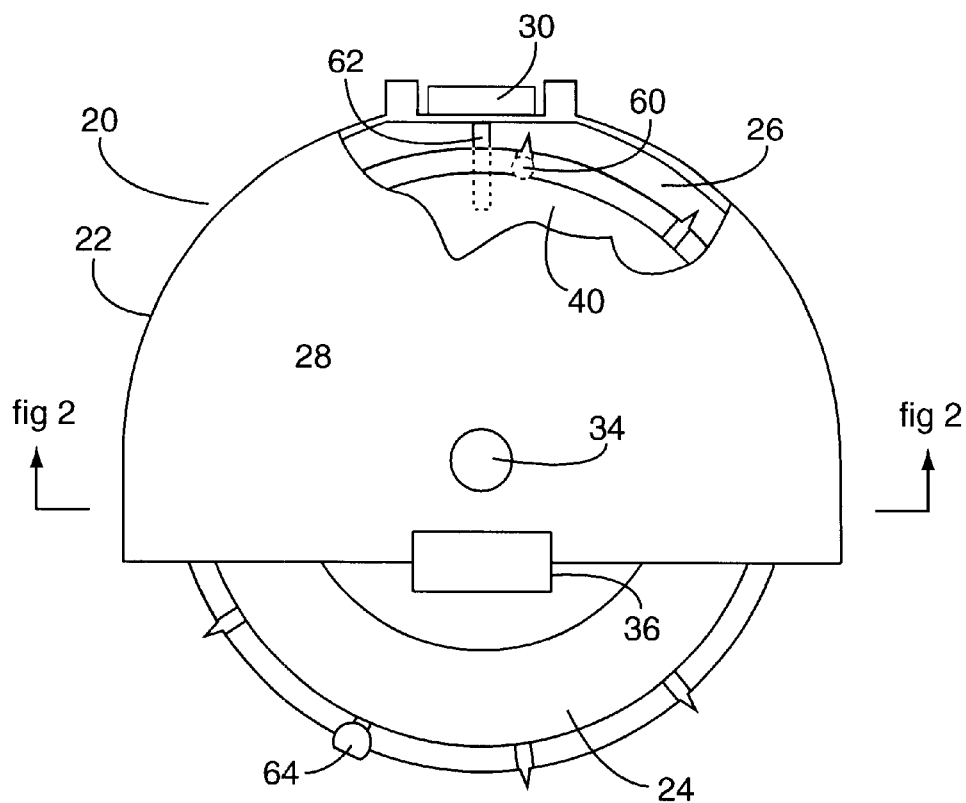
FIG. 1 is a side view of a skin testing device in accordance with the present invention with the cover shown in a closed position.
Figure 2:
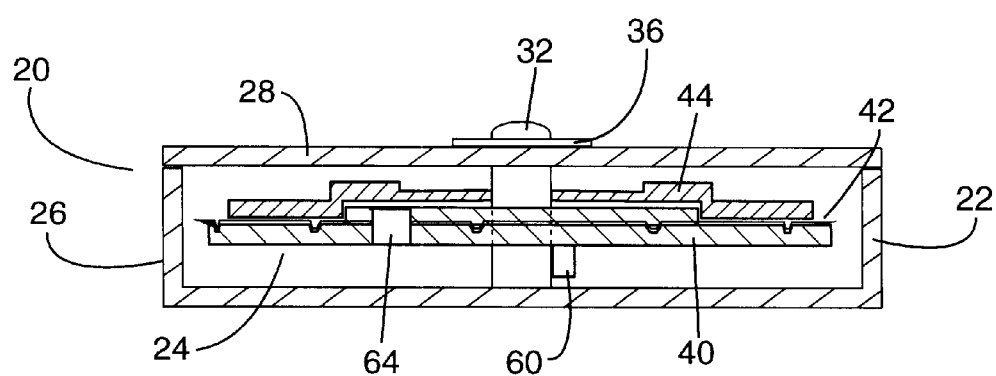
FIG. 2 is a bottom view of the skin testing device of FIG. 1.
Figure 3:
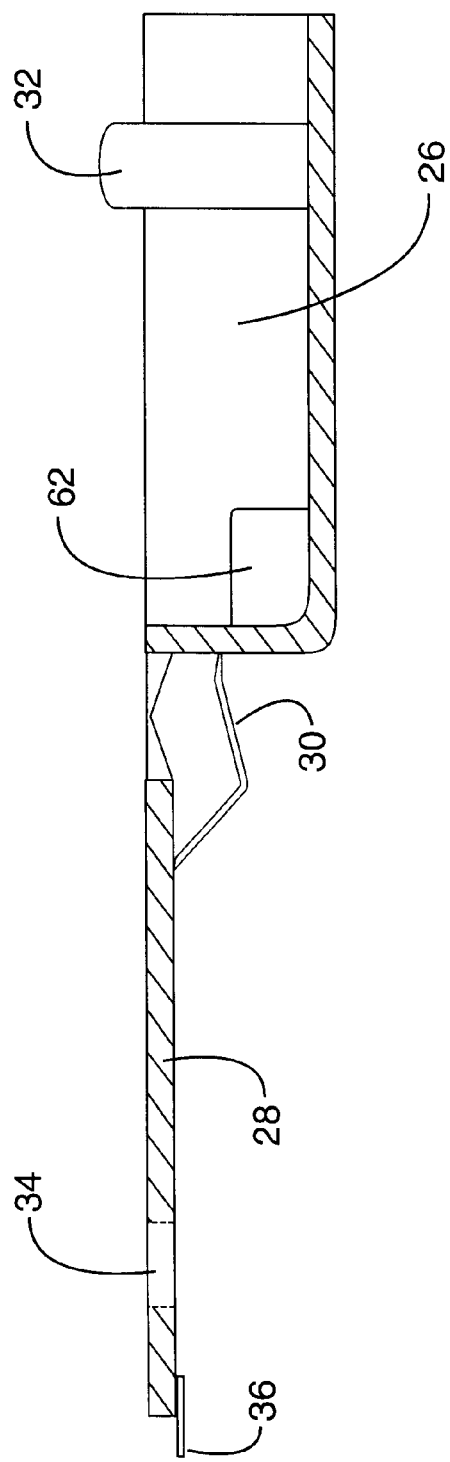
FIG. 3 is an end view of the housing for the skin testing device of FIG. 1 with the cover shown in an open position.
Figure 4:
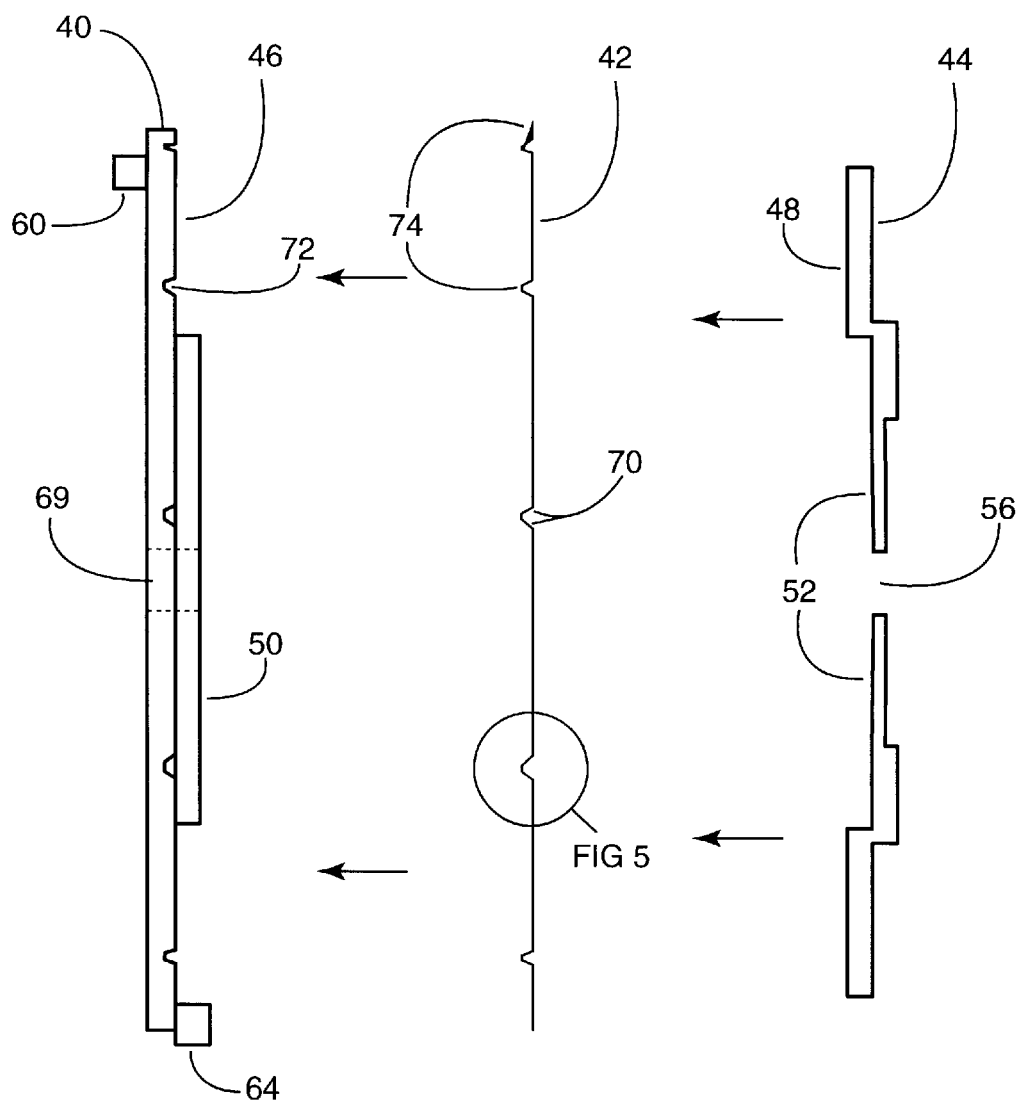
FIG. 4 is an exploded view of the wheel for the skin testing device of FIG. 1.

Referring to FIGS. 1–3, it may be seen that housing 22 has a semi-cylindrical body 26 that is connected to a corresponding semicircular cover 28 with a hinge 30. Hinge 30 is preferably a living hinge integrally formed with body 26 and cover 28. Body 26 and cover 28 thus define a hollow space having an open end for receiving wheel 24.

An axle pin 32 is integrally formed in body 26 to rotatably support wheel 24 as described further below. Axle pin 32 protrudes beyond the exposed circumferential edge of body 26. Cover 28 includes an aperture 34 that snugly receives axle pin 32 when cover 28 is moved into a closed position over body 26 as shown in FIG. 1. A finger tab 36 is located along an edge of cover 28 to facilitate moving cover 28 from a closed position as shown in FIG. 1 to an open position as shown in FIG. 3. This allows wheel 24 to be removed and a replacement wheel 24 to be inserted into place as described further below.

Referring to FIGS. 4–8, it may be seen that wheel 24 includes a support disk 40, an allergen plate 42, and a locking disk 44. Support disk 40 and locking disk 44 are preferably formed of plastic while allergen plate 42 is preferably formed of surgical steel.

Figure 8:
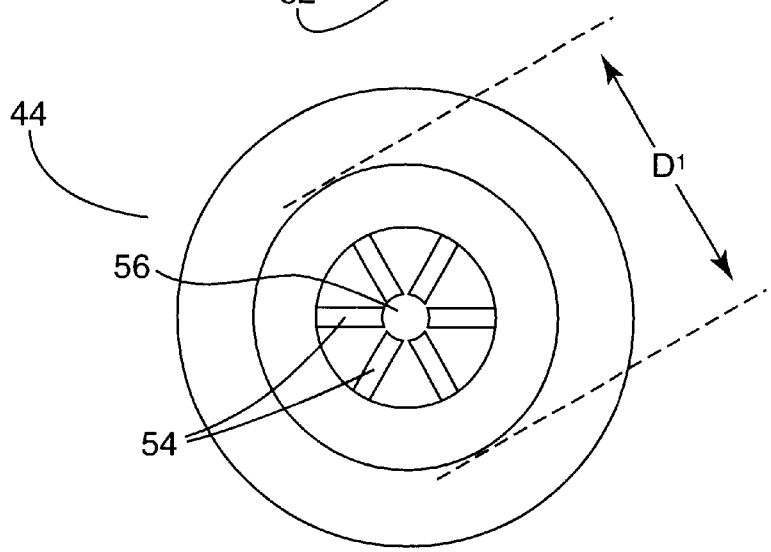
FIG. 8 is a plan view of the locking disk for the wheel of FIG. 4.

Allergen plate 42 is sandwiched between a first engaging face 46 on support disk 40 and a second engaging face 48 on locking disk 44. Support disk 40 and locking disk 44 are connected to each other by a friction fit with male member 50 on support disk 40 engaging female member 52 on locking disk 44. Female member 52 has a diameter D1 (see. FIG. 8) that is sufficiently larger than male member 50 which has a diameter D2 (see FIG. 6) to permit a friction fitting. Allergen plate has an aperture 53 with a diametric D3 (see FIG. 7) that is larger than diameter D2 of male member 50. Locking disk 44 includes radial arms 54 that define an aperture 56 for rotatably receiving and gripping axle pin 32.

Support disk 40 includes a pin 60 protruding from its outer face for engaging a rib 62 defined on an inner surface of body 26 of housing 22 (see FIG. 1). Pin 60 prevents wheel 24 from rotating beyond one revolution during use. A guide tab 64 protrudes from the circumferential edge of support disk 40 generally diametrically opposite to pin 60. Guide tab 64 defines a starting and finishing point to guide a user in operating device 20. Support disk 40 also defines an aperture 69 for rotatably receiving axle pin 32.

Allergen plate 42 has a plurality of first radial grooves 70 defined in one surface. First radial grooves 70 are formed to be received and supported by corresponding second radial grooves 72 defined on support disk 40. Pointed tines 74 are defined along the circumferential edge of allergen plate 42 in line with each first radial groove 70. Pointed tines 74 are generally planar and extend from the base 76 of each first radial groove 70.

Figure 5:
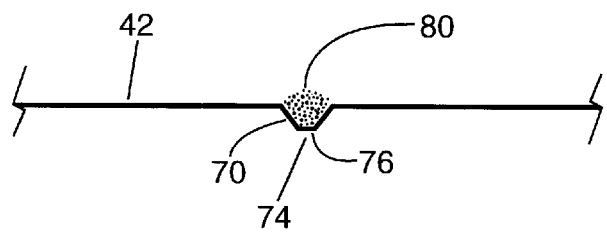
FIG. 5 is an enlarged end view of the allergen plate for the wheel of FIG. 4 showing an allergen solution disposed in the first radial groove.
Figure 6:
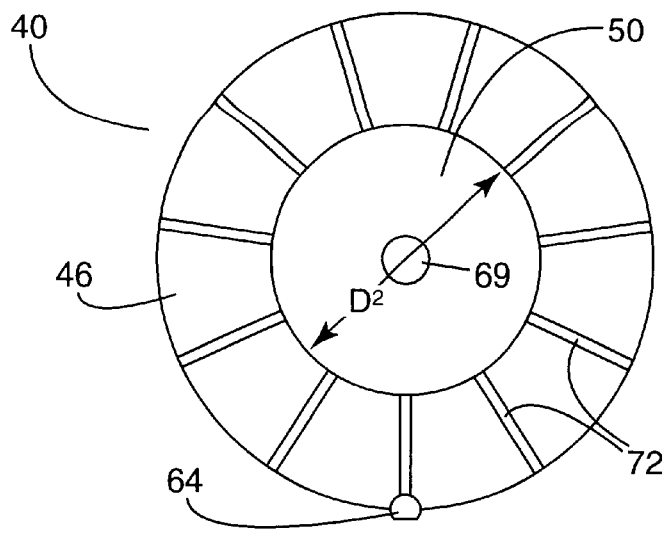
FIG. 6 is a plan view of the support disk for the wheel of FIG. 4.
Figure 7:
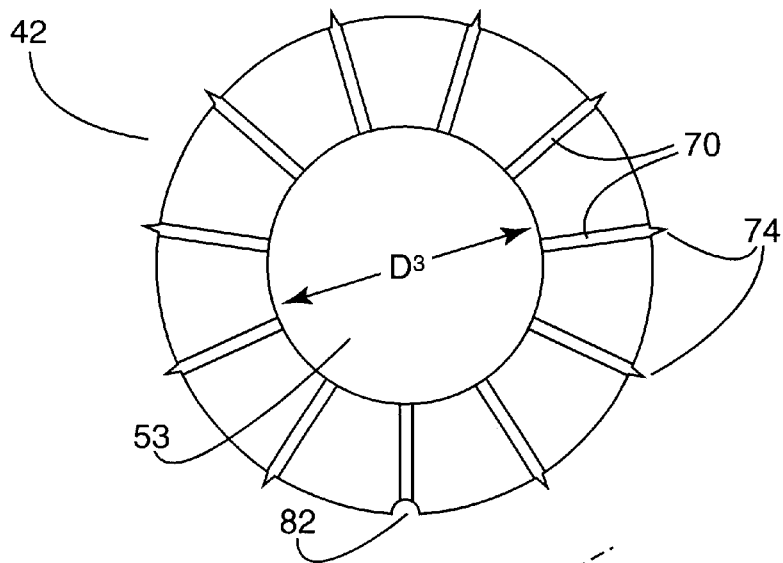
FIG. 7 is a plan view of the allergen plate for the wheel of FIG. 4.

First radial grooves 70 thus define a region for receiving an allergen solution 80 that is subsequently lyophilized as shown in FIG. 5. The shape of each first radial groove 70 prevents an allergen solution 80 from one groove 70 from mixing with a different allergen solution 80 from another groove 70. The allergen solution 80 is also deposited on each tine 74 due to the location of each tine 74 at the base 76 of each first radial groove 70. This construction of allergen plate 42 thus allows allergen solutions 80 to be deposited accurately and relatively easily on each allergen plate 42. A locating aperture 82 is defined in the plate 42 for aligning with guide tab 64 on support disk 40. This ensures that allergen plate 42 is supported in wheel 24 with allergen solutions 80 arranged in a predetermined order.

In use, a doctor or nurse would position skin testing device 20 on a patient's arm with guide tab 64 resting on the patient's skin and with pin 60 positioned on one side of rib 62. The device 20 is then moved along a patient's arm so that the wheel 24 rotates about axle pin 32. Each tine 74 penetrates the patient's skin sufficiently to introduce allergen solution 80 deposited on each tine 74 into the patient's skin. Once wheel 24 has completed a full revolution, pin 60 engages rib 62 and prevents any further rotation of wheel 24 in the same direction. The order of allergen solutions 80 deposited on allergen plate 42 is predetermined and the doctor or nurse is thus able to identify whether the patient is having allergic reactions to any specific allergen Once the test is complete the doctor or nurse opens cover 28 and removes wheel 24 so that it may be thrown away or recycled. A new, uncontaminated wheel 24 is then inserted on the device 20 for the next test.

Figure 9:
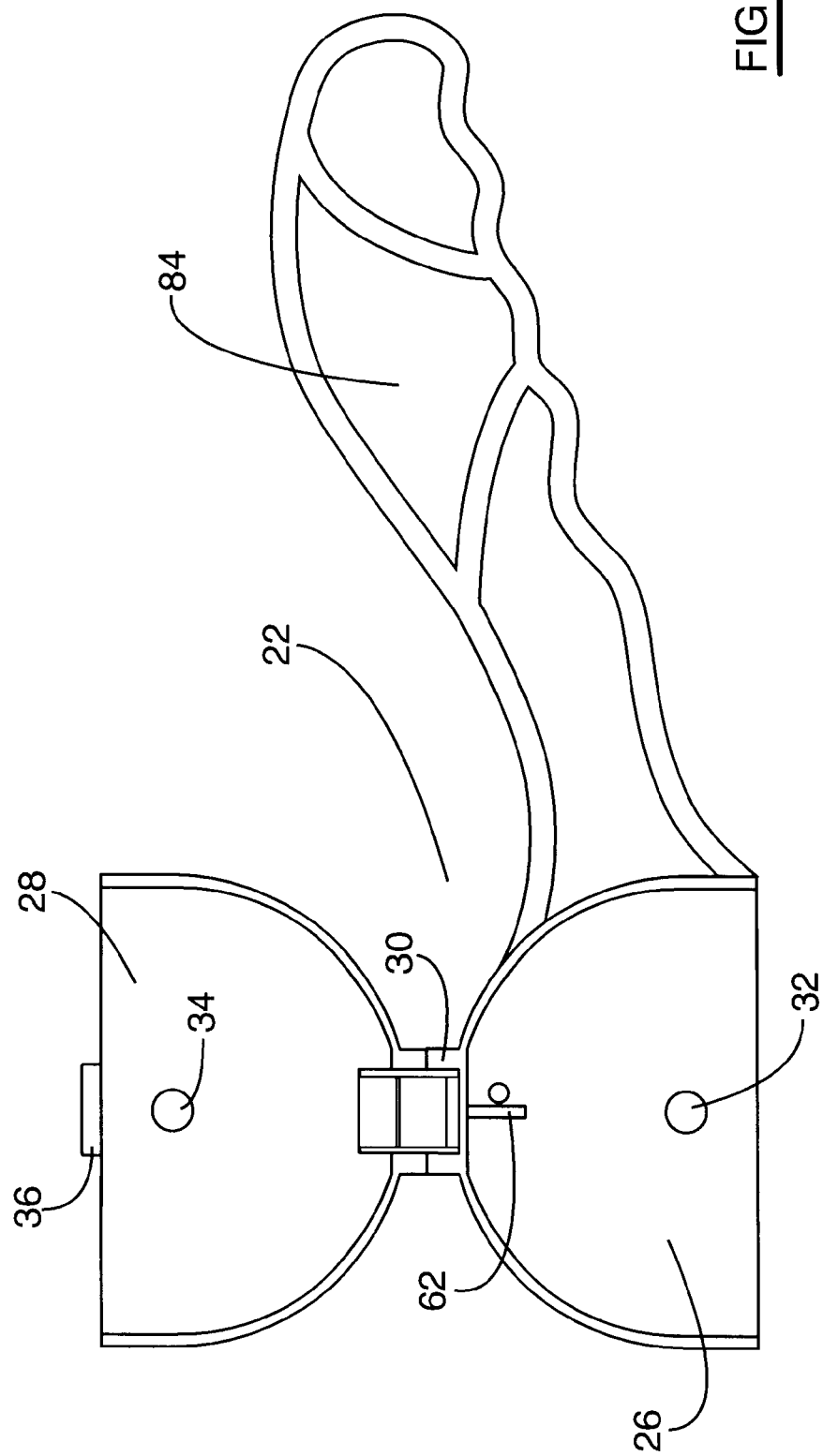
FIG. 9 is a perspective view of a second embodiment of a housing for a skin testing device in accordance with the present invention.

A second embodiment of housing 22 is shown in FIG. 9 where a handle 84 is integrally connected to body 26. Handle 84 allows operation of device 20 in a manner that reduces the likelihood of a user's hands being pricked by wheel 24.

It is to be understood that what has been described is a preferred embodiment to the invention. It can be appreciated that variations to this invention would be readily apparent to those skilled in the art, and this invention is intended to include those alternatives. For example, axle pin 32 may be integrally formed as part of wheel 24 (for instance as part of support disk 40) instead of part of body 26. Body 26 would then require a second aperture similar to aperture 34 for supporting axle pin 32.

I claim:

1. A skin testing device comprising:
    an allergen plate defining a plurality of pointed tines for piercing a patient's skin;
    a plurality of grooves defined in a surface of said allergen plate, each one of said grooves shaped to define a cavity for receiving an allergen solution, and each one of said grooves being aligned with a corresponding one of said pointed tines;
    a housing for shrouding a portion of said allergen plate;
    means for rotatably supporting said allergen plate within said housing.

2. A skin testing device as claimed in claim 1 wherein each of said pointed tines extends from the base of each of said grooves.

3. A skin testing device as claimed in claim 1 wherein said allergen plate is removably supported in said housing with said support means.

4. A skin testing device as claimed in claim 1 wherein said allergen plate is formed of surgical steel.

5. A skin testing device as claimed in claim 1 wherein said allergen plate is circular and wherein said grooves extend radially inwardly from said respective pointed tines.

6. A skin testing device as claimed in claim 1 wherein said allergen plate is sandwiched between a support disk and a locking disk to form a wheel, said wheel being supported in said housing with said support means.

7. A skin testing device as claimed in claim 6 wherein said support disk includes a plurality of second grooves arranged to receive said first grooves of said allergen plate to prevent said allergen plate from rotating relative to said support disk and said locking disk during use.

8. A skin testing device as claimed in claim 6 further comprising a pin disposed on said wheel and a rib disposed on said housing, said pin and said rib being sized to engage one another to prevent said wheel from rotating beyond one full revolution during use.

9. An allergen plate for a skin testing device comprising:
    a body defining a plurality of pointed tines for piercing a patient's skin; and
    a plurality of grooves defined in a surface of said body, each of said grooves shaped to define a cavity for receiving an allergen solution, and each of said grooves being aligned with one of said pointed tines.

10. A skin testing device as claimed in claim 9 wherein said pointed tines extend from the base of each of said grooves.

11. A skin testing device as claimed in claim 9 wherein said allergen plate is removably supported in said housing with said support means.

\* \* \* \* \*